United States Patent [19]

Kimbell et al.

[11] Patent Number: 5,255,074
[45] Date of Patent: Oct. 19, 1993

[54] CONCENTRATION MEASURING APPARATUS AND CALIBRATION METHOD

[75] Inventors: Chris L. Kimbell; Robert M. Hayman; W. Jay Szinyei, all of Houston, Tex.

[73] Assignee: Baker Hughes, Inc., Houston, Tex.

[21] Appl. No.: 686,776

[22] Filed: Apr. 17, 1991

[51] Int. Cl.⁵ .................. G01N 21/47; G01N 21/55
[52] U.S. Cl. ................... 356/445; 356/402; 356/446; 356/448
[58] Field of Search ............... 356/445–448, 356/402, 437, 436

[56] References Cited

U.S. PATENT DOCUMENTS

| 4,127,780 | 11/1978 | Kimbell | 356/448 X |
| 5,039,491 | 8/1991 | Saaski et al. | 356/446 X |

FOREIGN PATENT DOCUMENTS

| 58-79141 | 5/1983 | Japan | 356/437 |
| 59-94022 | 5/1984 | Japan | 356/402 |

Primary Examiner—Vincent P. McGraw
Attorney, Agent, or Firm—Alton W. Payne

[57] ABSTRACT

A concentration measuring apparatus is provided having a fluid sensing means, an optic transmission means, a signal processing means, and an interface means. The fluid sensing means comprises a reflective sensing media in a self-contained cassette. The cassette is operationally associated with a sample chamber. The cassette advances the reflective sensing media by a motor which is driven by the signal processing means. The optic means comprises a fiber optic line which is partially associated with a lamp and partially associated with a photocell. Light having a wave length in a specified range originates from the lamp, passes through a portion of the fiber optic cable and is cast upon the reflective sensing media. The altnerate portion of the fiber optic cable receives the reflected light from the reflective sensing media for transfer to the photocell. A signal is generated by the photocell representative of the change of reflectivity of the light from the reflective sensing media. The signal from the photocell is accepted by the signal processing means. The signal processing means contains an amplifier, an analog to digital converter, a computer and associated controls. The interface means is associated with the signal processing means. The interface means comprises a display, a 4-to-20 milliamp card and remote, explosion-proof switches for operator interaction with the concentration measuring apparatus. Also, the interface means is the link to an outside printer, an outside analog recorder as well as an outside host computer.

4 Claims, 7 Drawing Sheets

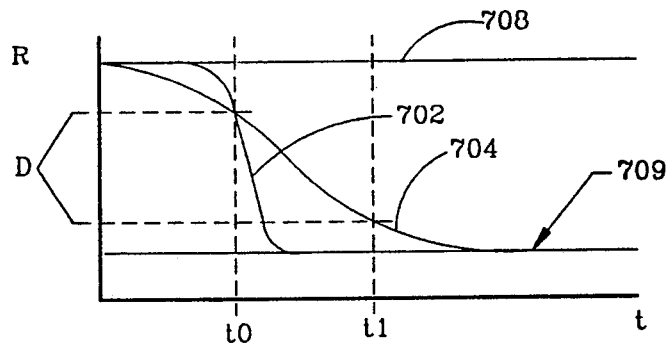
FIG. 10
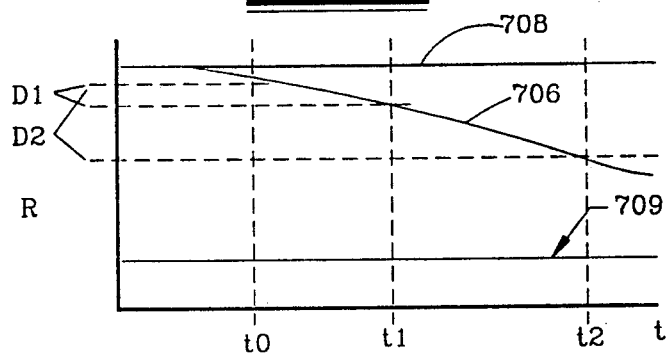
FIG. 11
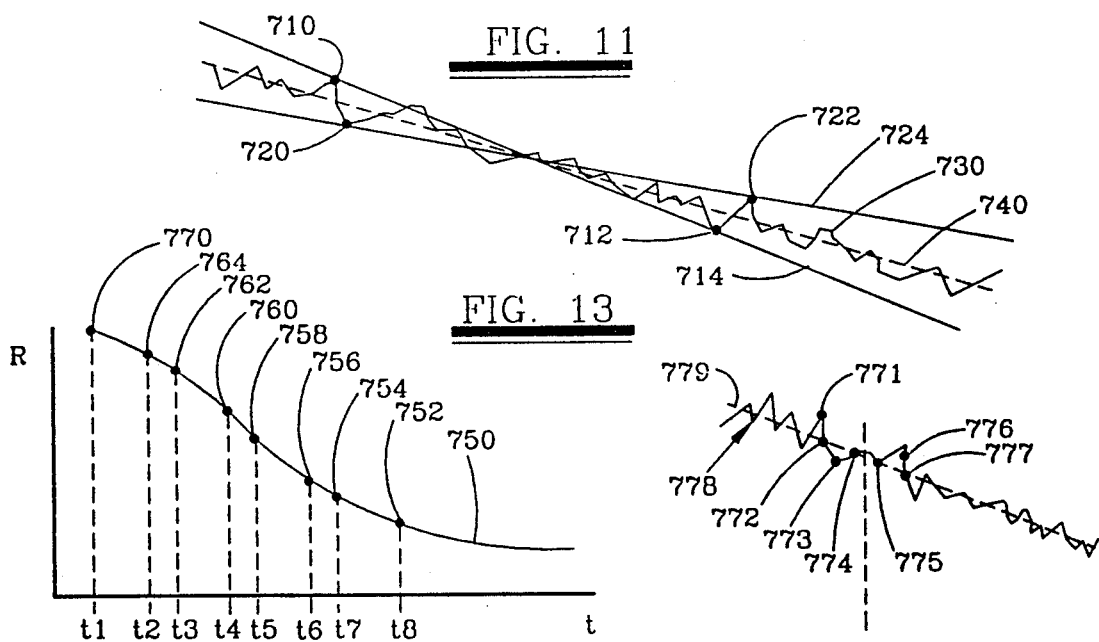
FIG. 13
FIG. 14
FIG. 15

CONCENTRATION MEASURING APPARATUS AND CALIBRATION METHOD

FIELD OF THE INVENTION

The field of the invention relates generally to an apparatus and method for detecting the concentration of a fluid. Specifically, the present invention relates to an apparatus and method for measuring sulphur, nitrogen and other compounds in a fluid.

BACKGROUND OF THE INVENTION

Chemical plants, oil refineries and other industrial facilities produce fluids which present health and safety problems. In some situations, even small amounts of the fluid, for example, a few parts per million or even a few parts per billion, can constitute serious health, safety and environmental problems. Also, such fluids and gases can be a danger to workmen in the vicinity of the facility. The difficulties in detecting and determining the presence of a selected fluid in a process stream or in the environment is exceedingly difficult due to the extensive nature and the large size of industrial plants.

Thus, the detection and monitoring of fluids associated with industrial plants is highly advantageous with respect to health, safety and environmental concerns. Further, the detection and monitoring of industrial fluids can prevent other dangers such as ignition, plant failure and the like.

Further, the need to detect particular constituents in a process stream can be based on product quality, process control, regulatory requirements and financial considerations. Particular fluid constituents of interest are, for example, hydrogen sulfide and nitrogen oxides. Industrial monitoring equipment exists for all phases of industry. Particularly, a variety of equipment is available using colorimetric methods. Colorimetric monitoring is utilized in process streams and associated atmospheres in and about industrial facilities. The colorimetric equipment and methods that are prevalent include absolute darkness techniques, tape difference techniques and analog first derivative techniques. Typically using colorimetric equipment, an ambient atmosphere is passed through the apparatus whereby the fluids in question react with a color-altering material. The magnitude of the color change is proportional to the concentration of the fluid in the atmosphere.

All colorimetric methods have problems. For example, absolute darkness techniques are subject to noise from zero fluctuation. The noise from zero fluctuations is due to the non-uniform reflectance characteristics of the colorimetric sensing media. Similarly, tape difference techniques require a zero reading. After the zero reading, a period of time must elapse between the initial reading and the final reading. The relatively long time period between readings does not take into account the nonlinearity of the sensing media and effects the response time of tape difference techniques. Analog first derivative techniques are subject to power line interferences. Further, analog first derivative techniques are limited by the current leakage in the differentiating capacitor which is typically used. Still further, the analog first derivative techniques operate in the linear portion of the response of the sensing device and require a linear response curve relationship for accurate results.

Many colorimetric analyzers generally have light sources, optics and detectors fixed in a rigid framework with light paths of the optics traversing through the ambient air. Such colorimetric analyzers require that correct alignment of the optical components be maintained during the operation of the equipment. The alignment of the optics is typically subject to environmental factors as well as mechanical problems. Examples of environmental and mechanical problems include changes in temperature, operation of equipment in high vibration environments, mechanical stress associated with typical equipment use, and the like.

Of additional concern is the environment in which the apparatus must operate. It is not unusual that the apparatus is required to be explosion proof for operation in industrial facilities. Typically, an explosion proof apparatus must be housed in a purged cabinet or housed in an explosion proof enclosure. The use of explosion proof equipment creates many problems with respect to adjustment, maintenance and calibration of the apparatus without compromising the protective environment of the explosion proof equipment.

It is, therefore, a feature of the present invention to provide an apparatus and method to monitor the concentration of a constituent in a fluid which eliminates or avoids the above discussed problems.

A feature of the present invention is to provide an apparatus and method whose measurement parameters can be changed or modified depending on the requirements of the particular analysis.

Another feature of the present invention is to provide a concentration measuring apparatus and method which utilizes a sliding derivative analysis technique.

Another feature of the present invention is to provide a concentration measurement apparatus and method that provides significant noise reduction and enhanced sensitivity.

Another feature of the present invention is to provide a concentration measuring apparatus and method which utilizes colorimetric sensing in conjunction with fiber optic means.

Another feature of the present invention is to provide a concentration measuring apparatus and method which is not effected by environmental changes, vibration and mechanical stress.

Yet another feature of the invention is to provide a concentration measuring apparatus and method which utilizes an operator interface that does not compromise explosion proof enclosures associated with such instruments.

Still another feature of the present invention is utilizing a colorimetric apparatus and method in association with a novel apparatus and method for the storage and dispensing of a reflective sensing media.

Still another feature of the present invention is utilizing a bifurcated fiber optic means that guarantees optical alignment and eliminates the need for periodic realignment.

Another feature of the present invention is to provide a concentration measuring apparatus and method which utilizes colorimetric techniques while providing that the lamp and electronics can remain in an explosion proof enclosure.

Another feature of the present invention is to provide a concentration measuring apparatus and method which utilizes colorimetric techniques including a single photocell system without the need for balancing of photocells.

Another feature of the present invention is to provide a concentration measuring apparatus and method that utilizes a specific wave length of light for increasing the contrast associated with the reflective sensing media and therefore increasing the sensitivity of the apparatus and method.

Yet another feature of the present invention is to provide a concentration measuring apparatus and method which utilizes magnetic switches for readily changing the operating parameters without compromising the explosion proof characteristics of the inventions.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features and advantages, and in accordance with the purpose of the invention as embodied and broadly described herein, a concentration measuring apparatus is provided comprising a fluid sensing means, an optic transmission means, a signal processing means, and an interface means.

Preferably, the fluid sensing means comprises a reflective sensing media in a self-contained cassette. The cassette is operationally associated with a sample chamber. The cassette advances the reflective sensing media by a motor which is driven by the signal processing means. Also preferably, the optic means comprises a fiber optic line which is partially associated with a lamp and partially associated with a photocell. Light having a wave length in a specified range originates from the lamp and if appropriate an optical filter, passes through a portion of the fiber optic line and is cast upon the reflective sensing media. Another portion of the fiber optic line receives the reflected light from the reflective sensing media for transfer to the photocell. A signal is generated by the photocell representative of the change of reflectivity of the light from the reflective sensing media. The signal from the photocell is accepted by the signal processing means.

Preferably, the signal processing means contains an amplifier, an analog to digital converter, a computer and associated controls. The signal processing means provides a unique data analysis technique. The analysis technique takes a first series of samples in rapid succession. The first samples are averaged. A specified period of time is allowed to elapse. A second series of samples is taken in rapid succession. The second series of samples are averaged. The averages or readings are used to determine a difference value. The difference value is converted into an intermediate value which is in engineering units. Multiple intermediate values are used to control alarms and related instrumentation. A final value is determined from the samples, readings and intermediate values representative of the total sensing media spot.

The interface means is associated with the signal processing means. The interface means comprises a display, a 4-to-20 milliamp card and switches for operator interaction with the concentration measuring apparatus. Also, the interface means is the link to an outside printer, an outside analog recorder as well as an outside host computer.

Also, a concentration measuring method is provided comprising a light source having a wave length responsive to the color characteristics of a reflective sensing media which changes color in the presence of a fluid, impinging the light on the reflective sensing media using ingressing optics, receiving the reflected light from the reflective sensing media using egressing optics, measuring the rate of change of the reflectance of the reflective sensing media and calculating the concentration of fluid based upon the rate of change of the reflective sensing media for the specified fluid.

BRIEF DESCRIPTION OF THE DRAWINGS

The accompanying drawings which are incorporated in and constitute a part of the specification, illustrate the preferred embodiments of the invention and together with the general description of the invention given above and the detailed description of the preferred embodiment given below, serve to explain the principles of the invention.

FIG. 10 is a graph illustrating the operation of the present invention outside the linear range and the operation of the present invention within the linear range of samples used in practicing the present invention;

FIG. 11 is a graph illustrating a portion of the range of darkness within the range between the maximum reflection and the minimum reflection of the reflective sensing media;

FIG. 13 illustrates an exploded view of examples of samples taken from the range of darkness measurement as illustrated in FIG. 11;

FIG. 14 is a graph illustrating readings derived from the samples taken for a single reflective sensing media spot in practicing the present invention;

FIG. 15 is an exploded view of a plurality of samples taken at one reading as illustrated in FIG. 14.

The above general description and the following detailed description are merely illustrative of the generic invention, and additional modes, advantages and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

Figure 1:
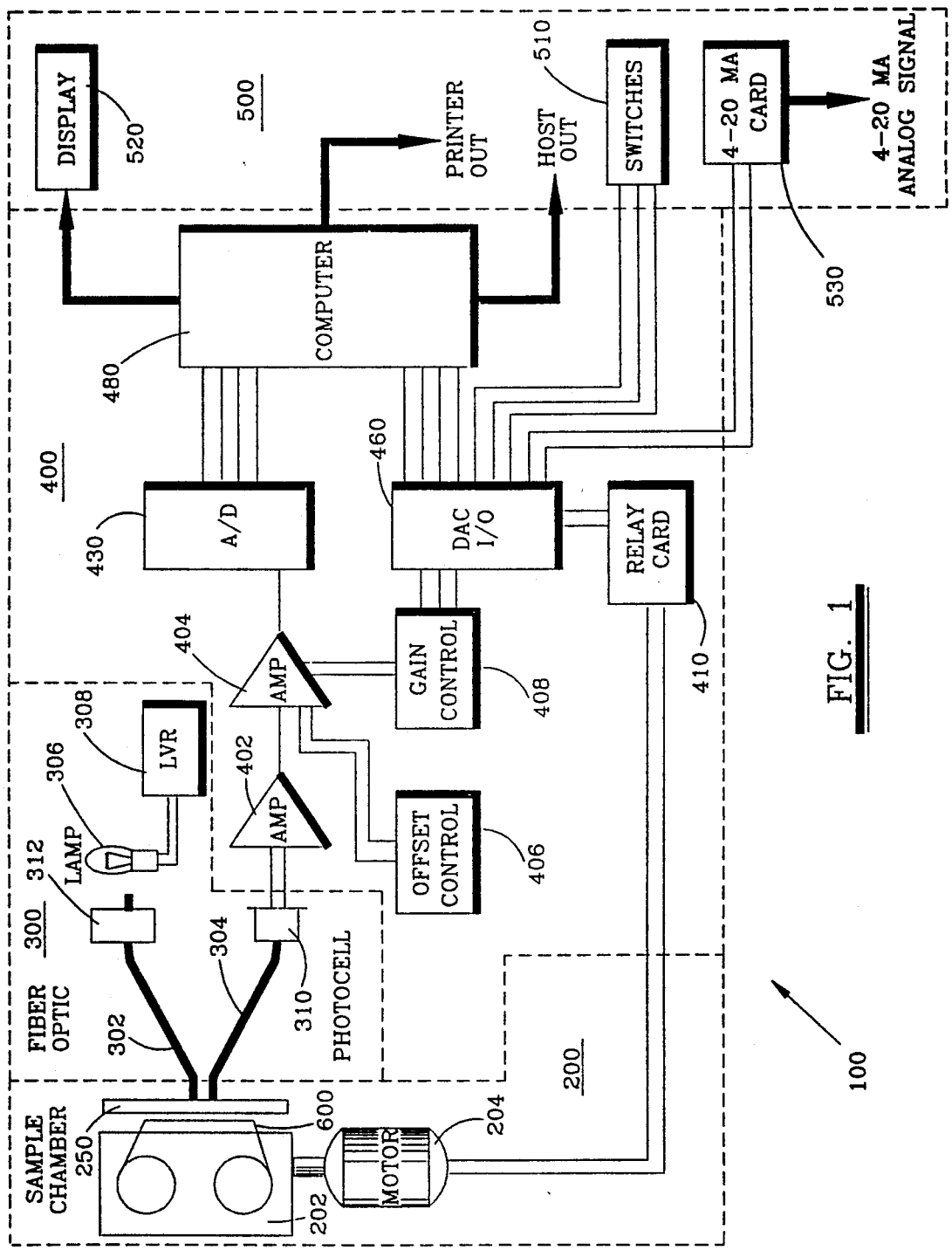
FIG. 1 is a schematic illustration of one embodiment of the concentration measuring apparatus and method of the present invention.

FIG. 1 is a schematic illustration of one embodiment of the present invention illustrating the fluid sensing means 200, the optic means 300, the signal processing means 400 and the interface means 500. The fluid sensing means 200 comprises a reflective sensing media cassette 202 in operative association with a sample chamber 250. The reflective sensing media cassette 202 is advanced using the motor 204. The motor 204 is controlled by the signal processing means 400.

The optic means 300 of the present invention comprises an ingressing optic 302, an egressing optic 304, a filter 312, a lamp 306, a lamp controller 308 and a photocell 310. The lamp 306 is controlled by the controller 308 for emitting light. The light is transferred to the ingress optic 302 which delivers the light to the reflective cassette 202 via the sample chamber 250. Prior to the light impinging upon the reflective sensing media 600 in the reflective sensing media cassette 202, a filter 312 is used. The filter 312 is used to be assured that the light received by the reflective sensing media 600 in the reflective sensing media cassette 202 is of the wave length which creates the most contrast for the reflective sensing media 600 after the reflective sensing media reacts with the fluid in the sample chamber 250. The egressing optic 304 receives the light reflected from the reflective sensing media in the reflective sensing media cassette 202 based upon the reflective sensing media's exposure in the sample chamber 250, and guides the light to the photocell 310. The photocell 310 constantly and continuously measures the intensity of the reflected light from the reflective sensing media in the reflective sensing media cassette 202.

The reflective sensing media 600 in the reflective sensing media cassette 202 is exposed to a fluid sample by means of the sample chamber 250. Using as an example hydrogen sulfide, the fluid analyzer 100 of the present invention can be used to measure the concentration of the hydrogen sulfide. The fluid analyzer 100 uses a chemically treated reflective sensing media 600 (See FIG. 4) that turns brown on exposure to hydrogen sulfide. (See U.S. Pat. Nos. 3,464,799 and 4,115,067 to Kimbell and Lyshkow, respectively) It is known that the rate at which the reflective sensing media turns brown is directly proportional to the concentration of the hydrogen sulfide in the sample passing through the sample chamber 250. (See U.S. Pat. No. 4,127,780 to Kimbell) The reflective sensing media 600 is exposed to the sample by means of the sample chamber 250. The sample chamber 250 has a "window" 252 (See FIG. 5) against which the reflective sensing media 600 is pressed to form a gas tight seal. The reflective sensing media 600 is exposed to sample gas within the window 252 (See FIGS. 5, 6, 7, 8 and 9 for the window 252). The upper portion of the sample chamber 250 is preferably made of a clear acrylic plastic. The window 252 is illuminated by a light having a specific frequency for creating a greater relative change of reflectivity between the color of the surface of the reflective sensing media 600 exposed to the fluid and the white surface of an unexposed reflective sensing media than would be had by unfiltered white light. For example, a brown spot made by exposing a lead acetate sensing media to blue light and hydrogen sulfide. The filter 312 which transmits only light in the range of wavelengths from approximately 415 nanometers to 540 nanometers is placed between a lamp 306 and the window 252 along the path of the ingressing optic 302. The light in the range of wavelengths from approximately 415 nanometers to 540 nanometers is guided to the appropriate portion of the reflective sensing media 600 in the window 252 using the ingressing optic 302. The light is reflected from the reflective sensing media 600. The reflected light is received by the egressing optic 304 to be directed to the photocell 310. As the reflective sensing media 600 progressively turns brown due to its exposure to hydrogen sulfide, the reflective sensing media 600 reduces in reflectance. The photocell 310 continuously measures the reflectance of the reflective sensing media 600. The photocell 310 generates an electrical signal. The electrical signal generated by the photocell 310 is directly proportional to the intensity of the reflected light. The signals for the photocell 310 are transferred to the signal processing means 400.

The signal from the photocell 310 is received by an amplifier 402. The amplifier 402 increases the magnitude of the received signal from the photocell 310. The magnified signal from the amplifier 402 is transferred to a second amplifier 404. The second amplifier 404 again increases the magnitue of the signal generated by the photocell 310. The second amplifier 404 is controlled by the offset control 406 and the gain control 408. The signal from the second amplifier 404 is sent to an analog-to-digital converter 430. The signal generated by the photocell 310 and amplified by the amplifiers 402, 404 is converted into a numerical value by the analog-to-digital converter 430. The digital values created by the analog-to-digital converter 430 are input into the computer 480.

The computer 480 provides that repeated readings of the reflective sensing media 600 reflectance throughout the sample analysis time are taken. Successive readings are subtracted from previous readings to calculate the rate of change of darkness of the reflective sensing media 600. The rate of change of darkness is combined with additional information stored in the computer 480. Typically, the additional information stored in the computer 480 is acquired from prior calibration runs for the apparatus of the present invention. The reading derived from the computer 480 is sent to the display 520 for viewing by an operator. Also, the reading may be sent an external printer or an external host computer. An analog representation is also calculated and the appropriate signal is sent to the DAC I/O board 460. The calculated value is compared with alarm values set by the operator. If the calculated value equals or exceeds the alarm value, the appropriate alarm relay on a relay card 410 is activated. When an analysis is complete, the tape advancement motor is operated by the relay card 410 and a new portion of the reflective sensing media 600 is drawn by the reflective sensing media cassette 202 into the window 252 of the sample chamber 250.

To maintain the complete explosion-resistant quality of the present invention, all critical components are securely enclosed. For example, the operation parameters associated with the apparatus of the present invention are set using the magnetic switches 510. The magnetic switches 510 are magneto-restrictive devices. The output of the magnetic switches drops to a low state when a magnet is brought within close proximity of the switch 510. The computer 480 "senses" the state of the switches 510. Typically, the switches 510 are operated at distances as far away as approximately one inch. The operation of the switches 510 through an explosion-proof glass cover in the explosion proof enclosure is greatly advantageous in not compromising the explosion-proof containment.

In the presently preferred embodiment of the invention, the display 520 is a liquid crystal display ("LCD"). The display 520 (See FIG. 3) comprises four lines 522, 524, 526 and 528. Each line 522, 524, 526 and 528 has a twenty character alpha-numeric display capability. The switches 510 are mounted in close proximity to the display 520. The bottom line of the display 520 is used to show the labels for each individual switch 510. The computer 480 is adaptable to change the function of the switches 510. The switches 510 can be activated depending upon the prompted input from the operator using a magnet in association with each switch 512, 514, 516 and 518 (See FIG. 3). During normal operation, in the present example of hydrogen sulfide, the display 520 shows percent of scale reflectivity, switch labels and other operational information. The magnetic switch 518 illustrated on right-hand side is labeled "reset" on the line 526 of display 520. Activating the magnetic switch 518 stops the analysis and shifts the display 520 to a menu of actions which can be chosen via the magnetic switches 510. Preferably, the actions available are calibrate, change settings, review settings, and normal.

Activating the "calibrate" switch 512 initiates the calibration procedure. During the calibration procedure, the operator will be asked for information concerning calibration units (for example, PPM, PPB and %), standard concentration, number of analyses during a calibration run, and the number of runs to be averaged into a final calibration value. Exiting from the "calibrate" menu starts the calibration running. Preferably, the parameters that can be changed by the operator using the magnetic switches 510 are the following: date, time, tape advance time (the amount of time the tape is moving during a tape spot change), readings per spot (the number of individual analyses to be made and averaged together for a sample before the tape spot is changed), analysis time (the time it takes to make an individual analysis), alarms, gain, printer on/off, 4–20 ma full scale, calibration concentration and units, e.g., PPB, PPM, %.

Figures 2A, 3:
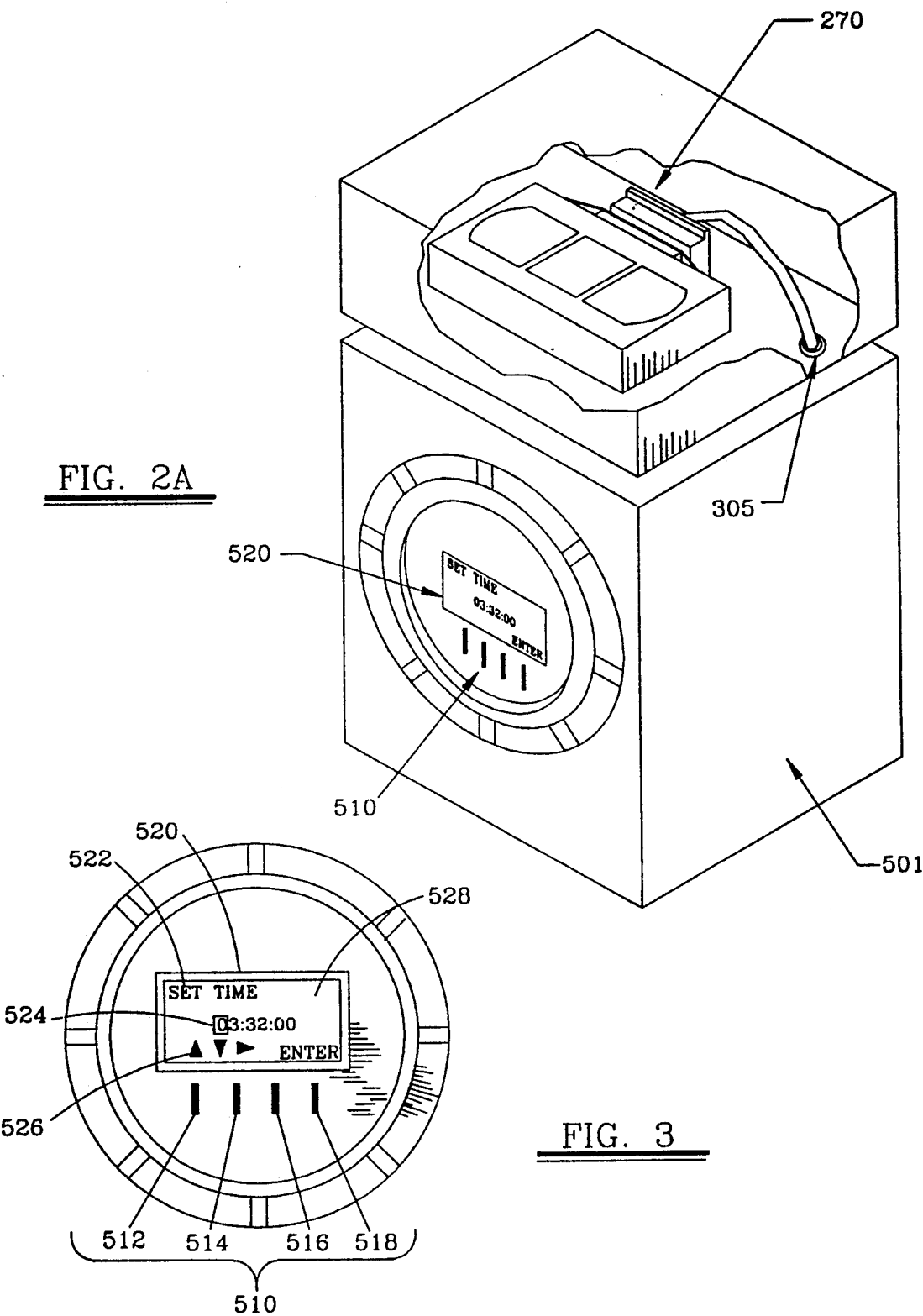
FIG. 2A is an illustration of the physical configuration of the reflective sensing media casette, explosion proof controls and fiber optics as practiced in one embodiment of the present invention.
FIG. 3 is an illustration of the explosion proof controls, illustrating an example read out, as practiced in one embodiment of the present invention.

FIG. 2A is an illustration of the relationship of the fluid sensing means 200, the optic means 300 (partial), the magnetic switches 510 and an explosion proof container 501. The fluid sensing means 200 is operationally associated with the explosion proof container 501 by the optic means 300. All information derived from the fluid sensing means 200 is transmitted and received by the optic means 300. The present system is completely controlled by the magnetic switches 510. The fiber optics 302, 304 egress the explosion proof container 501 via an explosion-proof feedthrough 305. The fiber optics 302, 304 engage an optic-sample interface 270. The optic-sample interface 270 connects the fiber optics 302, 304 to the reflective sensing media 600 via the cassette 202 and the sample chamber 250.

Figure 2B:
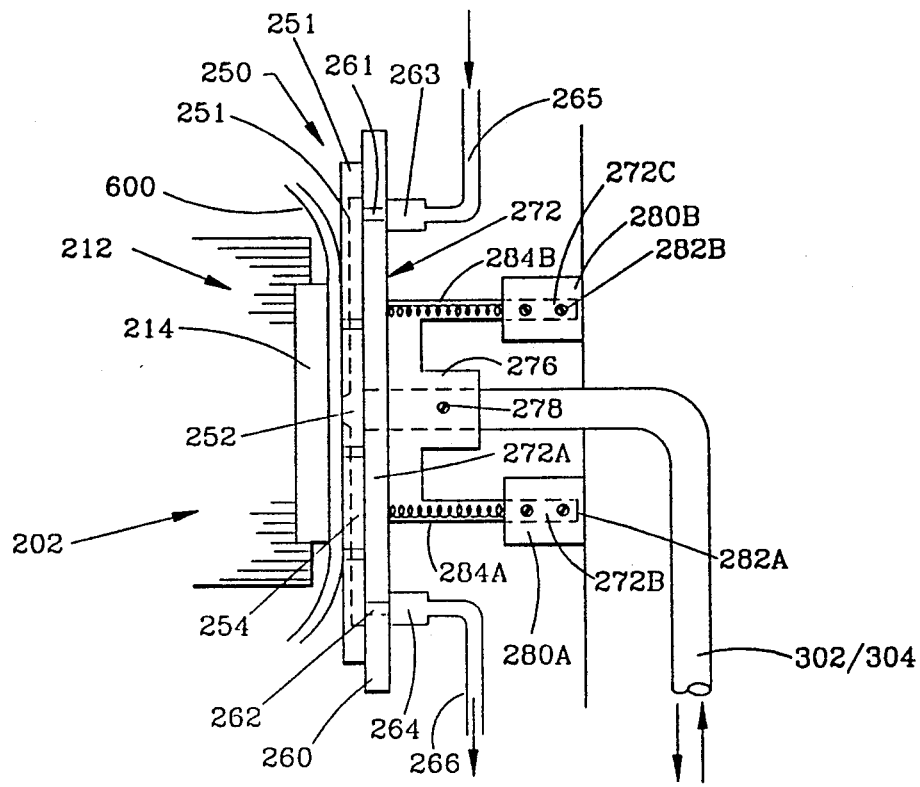
FIG. 2B is a partial cross-sectional view illustrating the physical configuration of the reflective sensing media, the cassette, the sample chamber and the fiber optics as practiced in the embodiment of the present invention illustrated in FIG. 2A.

FIG. 2B is a partial, cross-section illustrating the physical configuration of the reflective sensing media 600, the cassette 202, the sample chamber 250 and the fiber optics 302, 304 as practiced in one embodiment of the present invention. The media cassette 202 is removably secured against the sample chamber 250 using the optic-sample interface 270. The cassette 202 has an extender 212 for positioning the reflective sensing media 600 remote from the cassette 202 proper. A compressor 214 provides a resilient force for securely engaging the reflective sensing media 600 against the sample chamber 250.

Specifically, the reflective sensing media 600 is engaged against the sample chamber 250 such that the window 252 is sealed by the reflective sensing media 600. The sample chamber 250 has a body 251 which is hollowed out to have a cavity 254. The body 251 has an open end directly opposite the window 252. A transparent member 260 engages the body 251 of the sample chamber 250 for securing all sides of the cavity 254 for creating an enclosure. The transparent member 260 has an input aperture 261 and an output aperture 262. Engaged with the input aperture 261 of the transparent member 260 is a socket 263. The socket 263 is operationally associated with an input fluid line 265. Similarly, the sample chamber 250 has associated with its output aperture 262 a socket 264 and a fluid exhaust line 266. Thus, the fluid enters the line 265 passes securedly through the socket 263 and through the input aperture 261 into the cavity 254. The fluid passes through the cavity 254, engaging the reflective sensing media 600, continuing through the output aperture 262 and exiting the exit line 266.

It is important to maintain a constant pressure between the reflective sensing media 600 and the sample chamber 250. If a constant pressure is not maintained, the cavity 254 will leak and an accurate measurement of the concentration of the fluid is not possible. In order to achieve the constant pressure between the reflective sensing media 600 and the sample chamber 250, the optic-sample interface 270 is required. In association with the sample chamber 250 is a support 272. The support 272 has a securing portion 272A and a channeling portions 272B, 272C. The securing portion 272A is removably engaged with the transparent member 260. The securing portion 272A has attached thereto a cylindrical securing member 276. The cylindrical securing member 276 accepts the fiber optics 302/304. The fiber optics 302/304 is removeably secured to the cylindrical securing member 276 via a securing means 278. The securing means 278 can be an Allen screw or the like. The channeling portions 272B, 272C of the support 272 operationally engage the respective receptacles 280A, 280B. Each receptacle 280A, 280B has therein a channel 282A, 282B, respectively. The channeling portions 272B, 282C of the support 272 slide into and out of the channels 282A, 282B in the receptacles 280A, 280B. As the channeling portions 272B, 272C slide into and out of the channels 282A, 282B, the relationship between the sample chamber 250 and the reflective sensing media 600 is changed. To acquire the proper amount of tension between the reflective sensing media 600 and the window 252 of the sample chamber 250, the respective springs 284A, 284B are used. The springs 284A, 284B engage the receptacles 280A, 280B and the securing portion 272A of the support 272. By using springs 284A, 284B having differing elasticities, different pressures can be adapted between the reflective sensing media 600 and the sample chamber 250.

FIG. 3 illustrates the explosion proof controls, and an example read out as practiced in one embodiment of the present invention. FIG. 3 is a blow up of the display 520 illustrated in FIG. 2. The liquid crystal display 520 is associated with the set of magnetic switches 510. The magnetic switches 510 comprise a first switch 512, a second switch 514, a third switch 516 and a fourth switch 518. Also, the liquid crystal display 520 comprises a plurality of display lines 522, 528, 524, 526 which can display various parameters and results depending upon the operation of the analyzer. One of the display lines 526 is associated with the switches 512, 514, 516, 518 and is dedicated solely to display labels for the switches 512, 514, 516, 518. The function of the display lines 522, 528, 524 changes with the operation of the analyzer. The display line 522 is sometimes used to display the parameters associated with the hydrogen sulfide version of the present invention which includes: date, time, time per reading, readings per spot, calibration concentration, units, gain, number of calibration readings to take, number of calibration readings to average, the low alarm value, the high alarm value, the tape advance time, the manual motor run time, the full scale value of the 4–20 milliamp board and printer on/off.

Figure 4:
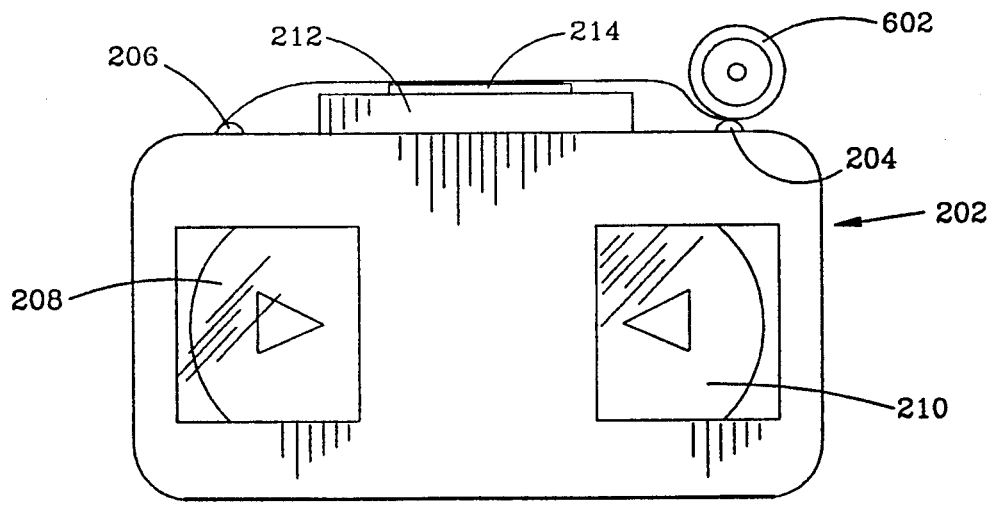
FIG. 4 is an illustration of the reflective sensing media cassette and driving capstan as practiced in one embodiment of the present invention.

FIG. 4 is an illustration of the reflective sensing media cassette 202 associated with the fluid sensing means 200. The reflective sensing media cassette 202 contains a reflective sensing media 600. The reflective sensing media 600 is spooled on the reel 208. A take up reel 210 is used. The reflective sensing media cassette 202 is generally designed as a typical VCR cassette. The reflective sensing media 600 on the reel 208 is passed over a guide 206, over an extender 212, over a compressor 214 of resilient material, around a second guide 204 and onto the take up reel 210. The compressor 214 pushes the reflective sensing means 600 against the sample chamber 250 providing a fluid tight seal at the sample chamber window 252.

Figure 5:
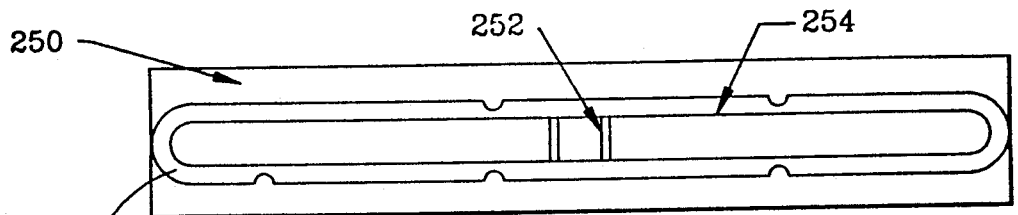
FIG. 5 is a plan view of one embodiment of the body of the sample chamber of the present invention.

FIG. 5 is a plan view of one embodiment of a body of a sample chamber used in practicing the present invention. The sample chamber 250 has associated therewith a cavity 254 and a fluid-media contact window 252. In one embodiment, the fluid-media contact window 252 is configured as a rectangle in the sample chamber 250.

Figure 6:
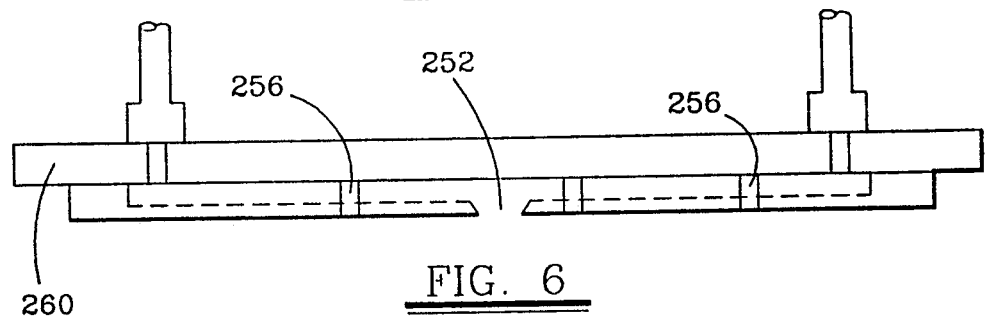
FIG. 6 is a cross-sectional view of the sample chamber body illustrated in FIG. 5 used in practicing the present invention.

FIG. 6 is a cross-sectional view of the sample chamber 250 illustrated in FIG. 5. The fluid-media contact window 250 comprises sides having at least one portion angled. Preferably, the inclined sides are at a 45° angle. One or more notches 256 are used to secure the sample chamber 250.

Figure 7:
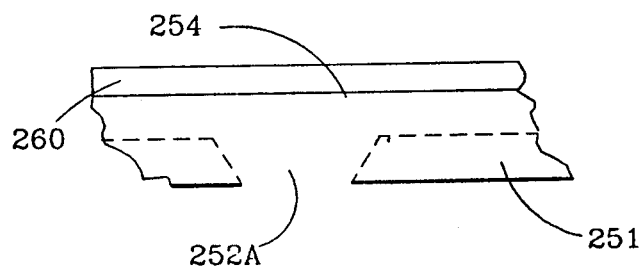
FIG. 7 is an exploded cross-sectional view of the open, gas-reflective sensing media contact aperture used in practicing the present invention.
Figure 8:
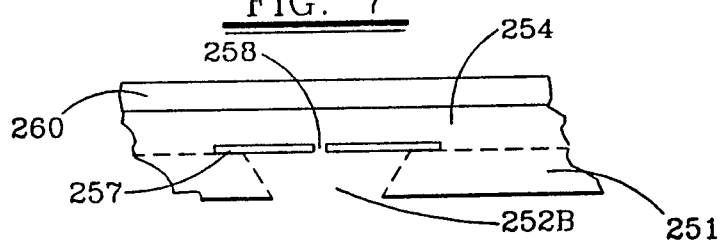
FIG. 8 is an exploded cross-sectional view of the diffusion-type, gas-reflector contact aperture used in practicing the present invention.
Figure 9:
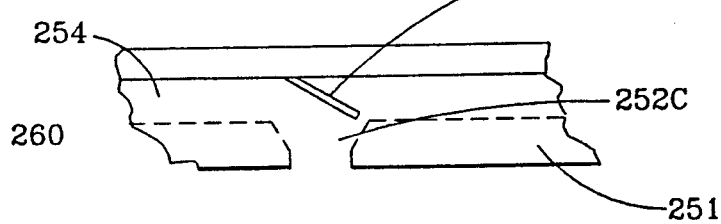
FIG. 9 is an exploded cross-sectional view of the wedge-type, gas-reflector contact aperture used in the present invention.

FIGS. 7, 8 and 9 are exploded cross-sectional views of open, diffusion and wedge window configurations 252A, 252B, 252C which are examples of those used in practicing the present invention. FIG. 7 is an exploded cross-sectional view of the open fluid-media contact window 252A. The fluid fills the cavity 254 and the open fluid-media contact window 252A at the same time. The reflective sensing media 600 (see FIG. 2B) secures the cavity 254 and reacts with the fluid passing through the cavity 254. The ingressing optic 302 and the egressing optic 304 are removeably affixed to the sample chamber 250 by a cylindrical securing member 276 mounted on a sample chamber support 272. The sample chamber support 272 also provides support for the sample chamber 250. The sample chamber support 272 holds the sample chamber window 252 in alignment with the ingressing optic 302 and the egressing optic 304.

FIG. 8 is an exploded cross-sectional view of the diffusion fluid-media window 252B used in practicing the present invention. The diffusion fluid-media window 252B restricts the flow of fluid engagement with the reflective sensing media 600. The diffusion fluid-media window 252B attenuates the sensitivity of the fluid sensing means 200 for providing a wider detection range than possible with the previously described open fluid-media contact window 252A. The diffusion fluid-media window 252B comprises a plate 257 parallel to the interface between the cavity 254 and the body 250. The plate 257 has a slot 258 located approximately at the radial axis of the window 252B. The size of the slot 258 is a function of the estimated concentration of the fluid and the operation parameters of the present invention. Depending on the measurement characteristics sought, generally, the larger the hole 258 the larger the concentration of fluid engaged with the reflective sensing media 600. Obviously other configurations and embodiments are evident and can be adapted within the scope of the present invention.

FIG. 9 is an exploded cross-sectional view of the wedge-type fluid-media window 252C used in practicing the present invention. The wedge-type fluid-media window 252C increases the flow of fluid engagement with the reflective sensing media 600. The wedge-type fluid-media window 252C enhances the sensitivity of the fluid sensing means 200 for providing greater sensitivity than possible with the previously described open fluid-media contact window 252A. The wedge fluid-media window 252C comprises a plate 259 angled to encompass all or a part of the cavity 254. The plate 259 is angled to place the downstream portion in the proximity of the window 252C and the body 250. The upstream portion of the plate 259 is in the proximity of the transparent member 260 (see FIG. 2B for a view of the transparent member 260). The size and angle of the plate 259 is a function of the estimated concentration of the fluid and the operation parameters of the present invention. Depending on the measurement characteristics sought. Obviously other configurations and embodiments are evident and can be adapted within the scope of the present invention.

FIG. 10 is a graph illustrating parameters inside and outside a linear range as practiced in the present invention. A curve 702 is illustrated whereby the readings are taken at time $t_0$ and time $t_1$. It is important to note that reading $t_0$ was taken at the beginning portion of the curve illustrated between the range of reflectances D. The graph illustrates reflectance on the ordinate and time on the abscissa. For the curve 702 and its associated counterpart curve 704, the portions lie between the range D of reflectance. To acquire readings in the portions of the curves, either the curve 704 must be used or the time between readings must be shortened for the other curve 702.

FIG. 11 is a graph with the reflectance as the ordinate and time as the abscissa. FIG. 11 illustrates a portion of the range of darkness or "detection window" within the useful range between the maximum reflectance and the minimum reflectance of a portion of the reflective sensing media. A curve 706 is plotted. Readings are taken at time $t_0$, $t_1$ and $t_2$. At each reading $t_0$, $t_1$ and $t_2$, the curve 706 is linear. The range of the useful portion of the curve 706 is between the time when the reflective sensing media is white 708 and the time when the reflective sensing media is completely darkened 709. When the reflective sensing media is in the range between no darkening and maximum darkening that multiple readings can be acquired from a particular reflective sensing media spot. The use of multiple readings at a particular reflective sensing media spot enhances the reliability of the measurements because multiple readings from the same spot are averaged. Between when the reflective sensing media 600 is white and when it turns dark, the multiple readings act to reduce noise and compensate for measurement nonlinearities. Additional processing could also be adapted for use in addition to averaging, for example without limitation, least squares, splines, filtering or other signal processing techniques.

Figure 12:
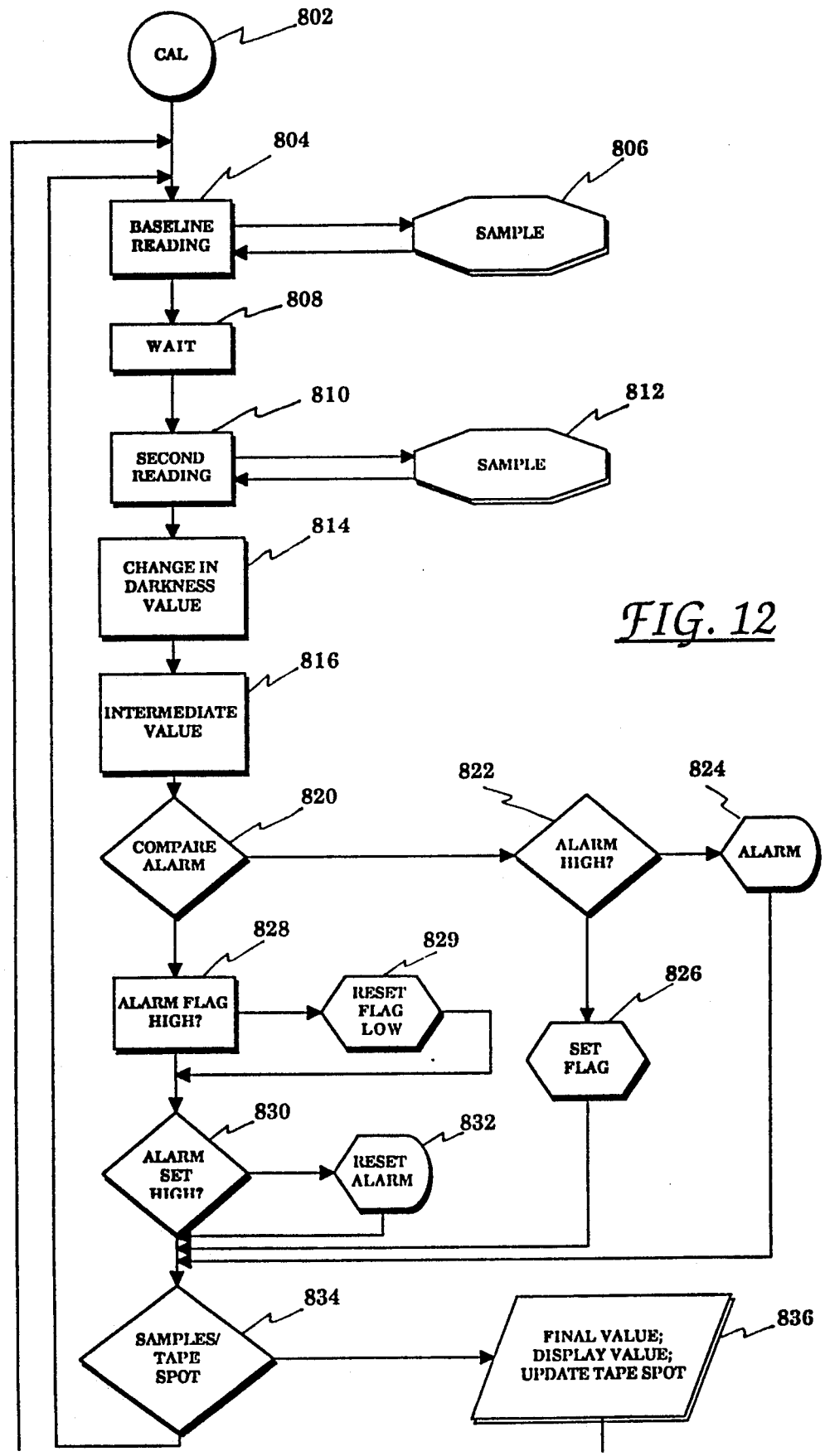
FIG. 12 is a flow diagram illustrating a typical measurement cycle as practiced in one embodiment of the present invention.

FIG. 12 is a flow diagram illustrating a typical measurement cycle as practiced in the present invention. The fluid analyzer 100 is calibrated (802). A first baseline reading is determined (804). The determination of the first baseline reading comprises taking a predetermined number of samples for the particular reading (806). For example, one embodiment of the present invention provides that seven samples are taken to establish data for a single reading. Preferably, the samples taken (806) are acquired in rapid succession. It can be appreciated that alternate embodiments may require that samples be taken in deliberate methods, including for example delayed sampling, patterned sampling and the like. After the specified number of samples are taken, the reading is calculated (804). The first baseline reading (804) is the average of the samples taken (806). A predetermined period of time is allowed to pass (808). A second intermediate reading is determined (810). The determination of the second intermediate reading (810) comprises taking a predetermined number of samples for the intermediate reading (812). Again in one embodiment, the samples are acquired (812) in rapid succession. After the specified number of samples are taken, the intermediate reading is calculated (810). The second intermediate reading (810) is the average of the samples taken (812). A change in darkness calculation is made (814). The change in darkness calculation (814) utilizes the first baseline reading (804), the second reading (810) and the predetermined period of time between readings (808). An intermediate value is determined (816) using the information acquired during calibration (802). The intermediate value (816) is in engineering units for ease of use by an operator. The intermediate value (816) is compared with a predetermined value. If the intermediate value (816) is greater than the predetermined value, a determination is made as to whether the alarm flag is set high (822). If the alarm flag is set high, the alarm sounds (824). If the prior alarm flag is not set high, the alarm flag is set high (826). Thereafter, a determination is made as to whether the number of samples per tape spot (834) has been reached. If the number of samples per tape spot (834) has not been surpassed, the technique requires that the method begins by determining yet another base line reading (804). If, after the intermediate value (816) is calculated and compared to a predetermined alarm value (820) if the intermediate value is less than the predetermined alarm value, a determination is made as to whether the alarm flag is set high (828). If the alarm flag is set high (828), the flag is reset to a low position (829). However if the alarm flag is not determined to be set high (828), then a determination is made as to whether the alarm is set high (830). If the alarm is set high, the alarm is reset low (832). After the alarm is reset low (832), a determination is made concerning whether the number of samples per tape spot has been achieved (834). If the alarm is not set high (830), then the determination is directly made concerning whether the number of samples per tape spot (834) has been achieved. If the predetermined number of readings per tape spot have not been achieved (834), the cycle is repeated. If the predetermined number of readings per tape spot (834) is surpassed, a final value is determined (836). The final value is the average of each of the prior intermediate values (816). The final value is displayed and a new sensing media spot is advanced into the window.

The methodology for making the calculations to determine the readings from the samples is important. FIG. 13 illustrates an exploded view illustrating examples of samples taken from the range of darkness measurements as illustrated, for example, in FIG. 11 and FIG. 12 (Specifically, see step 814). One objective of the present analysis is to determine the slope of the actual line 740. The measured line 730 is illustrated as a jagged line. A sample is taken at a point 710. Another sample is taken at a point 712. The slope of the measured line between the sample points 710, 712 is the difference of the points divided by the time, i.e., $$\text{slope} = \frac{R_{712} - R_{710}}{\Delta t}$$

Another example of sample points measured in an effort to determine the actual line 740 is to measure a sample point 720 and another sample point 722. A line 724 drawn through the sample points 720, 722 is illustrated. Similarly the slope of the line 724 is known to be $$\text{slope} = \frac{R_{722} - R_{720}}{\Delta t}$$

Obviously, neither the line 714 nor the second line 724 is an accurate representation of the slope of the true line 740. It is desirable to derive a method for measuring, as closely as possible and as accurately as possible, the true line 740. It has been determined that acquiring rapid samples in succession and averaging the samples to determine an average reading enhances the accuracy of each reading. Similarly, the average of each reading can be averaged to better determine the change in darkness value associated with the line 740. The technique of the present invention provides a better approximation to a noise free line than heretofore achievable.

FIG. 14 is a graph of the reflectance on the ordinate and time on the abscissa illustrating five readings taken for a single reflective sensing media spot. At each time, from $t_1$ through $t_8$, a rapid succession of sample points are taken. The rapid succession of sample points provides an average reading at each point which is very close to the actual point on the "real" line.

As an example of the operation of the present invention, FIGS. 13, 14 and 15 are used. The reflective sensing media 600 is updated in the sample window 252 of the sample chamber 250 in the analyzer 100. The reflective sensing media spot is exposed to a fluid; hydrogen sulfide, for example. The media 600 exposed to the fluid through the window 252 of the sample chamber 250 will be affected by the fluid. The reflective sensing media spot, defined by the window 252, begins darkening due to its exposure. At time $t_1$, seven samples are taken in rapid succession in practicing one embodiment of the present invention. However, it is understood that a different number of sample points may be appropriate for different situations, e.g., 12 sample points, 15 sample points, etc. From the seven sample points, the reading 770 is determined. These seven sample points 770 are illustrated in FIG. 15. FIG. 15 is an exploded view of the plurality of sample points taken at $t_1$ as illustrated in FIG. 14. The sample points 771, 772, 773, 774, 775, 776 and 777 are illustrated taken at time $t_1$. The data line 778 is illustrated as the jagged line and the "actual" line 779 is illustrated as a dashed line. The seven sample points illustrated in FIG. 15 taken at time $t_1$ are averaged together. The average of the sample points taken at time $t_1$ is $R_{t1(avg)}$. Thus, $R_{t1(avg)}$ is an approximation of $R_{t1}$. The value of $R_{t1(avg)}$ is an approximation of the value if the reflectance reading is taken at time $t_1$ from a noise free signal. An interval of time $(t_2-t_1)$ is allowed to pass. At time $t_2$, seven more sample points 764 are taken in rapid succession. The sample points 764 are averaged together to give $R_{t2(avg)}$. The $R_{t2(avg)}$ is an approximation of what $R_{t2}$ would be if the reflectance reading was taken at time $t_2$ from a noise free signal. Additional readings 762, 760, 758, 756, 754 and 752 are taken at their respective times, $t_1$, $t_2$, $t_3$, $t_4$, $t_5$, $t_6$, $t_7$, and $t_8$.

The derivative of such samples with respect to time is equal to the concentration of the fluid, e.g., hydrogen sulfide, at the tape spot for a constant sample flow. An approximation of the derivative of the reading with respect to time can be made using $$\frac{\Delta R}{\Delta t}.$$

$$\frac{\Delta R}{\Delta t}$$

can be expressed as follows:

$$\frac{\Delta R}{\Delta t} = \frac{R_{t1(avg)} - R_{t2(avg)}}{t_2 - t_1}$$

The use of the approximation of the derivative of the reading with respect to time establishes one particular reading on the tape reflective sensing media spot. This particular reading on the reflective sensing media spot is referred to as an intermediate value. Subsequent values, processed as described herein, are taken at the different time periods illustrated in FIG. 14.

Although the change in reflectance with respect to time is almost linear, sufficient nonlinearity exists that the values from reading to reading on a given reflective sensing media spot are significantly different. After the predetermined number of samples on a given reflective sensing media spot have been made, the intermediate values are averaged together to form a final value for that particular reflective sensing media spot. The final value is then displayed on the display 520 or printed out to a printer. The reflective sensing media is advanced and the measurement precess is repeated.

It is important to note that if a reading was all that was being sought, other methods of data collection and analysis would be appropriate, for example, least squares. In the case of a least squares analysis, the total analysis time for a given reflective sensing media spot could be two minutes. Readings would be taken throughout the two minute measurement interval. After the measurement interval, the slope of the best fit line through the data would be determined. The slope would be the least squares fit the derivative of the readings with respect to time. Alarms could be keyed to the least squares analysis, but updates to alarms status could occur only at two minute intervals. Using such long time analysis before setting alarms is an extreme fallacy in prior analysis techniques. The present invention overcomes such analysis faults.

In the presently preferred embodiment of the invention, the analysis time and the number of intermediate values per spot are controlled by the operator. Also, the analysis time and the number of intermediate values per spot can be varied depending upon the particular application. Intermediate value times can be as short as one second per value or as long as ninety-nine seconds per value. Also, the number of values per spot can be varied.

The alarm sequence utilized in the present invention for hydrogen sulfide is two intermediate values. The first value above the alarm setting alerts the computer of a possible alarm situation. The computer monitors the second consecutive intermediate value. If the next intermediate value is above the alarm setting, the computer sets the alarm relay and annunciates the alarm on the display, and possibly the printout. The computer continues to monitor consecutive intermediate values for one that is below the alarm setting. When a sample is encountered that it below the alarm setting, the computer resets the alarm relay. For typical process analyzers utilizing hydrogen sulfide, alarm response is important. Alarm levels are keyed to the intermediate values and not to the final average value for each reflective sensing media spot. For example, a set up where analysis times are twenty seconds and there are six readings per reflective sensing media spot, the total read time per spot is two minutes. However, each intermediate reading is twenty seconds. The alarm status is checked as often as every forty seconds, i.e., each two intermediate readings, instead of every two minutes.

The analysis of the present invention provides multiple samples being taken about the reading of interest. The multiple samples are averaged in an attempt to get a value representative of a noise free reading. The reading value is used in the calculation of slopes. Multiple intermediate readings are taken for each reflective sensing media spot. The multiple intermediate readings are averaged to get the displayed final value. This procedure reduces noise and provides that minor differences in linearity of the intermediate readings are more accurate. Alarms are based on two intermediate readings. Alarms are not based on the average final value per reflective sensing media spot. Basing the alarms on two consecutive intermediate readings provides rapid indication of an alarm condition.

The analyzer 100 measures the rate of change of darkness of the reflective sensing media 600. For example, in the case of lead acetate being used as the media 600, a finite degree of darkness can be attained before all the lead acetate is chemically reacted with the fluid sample, for example hydrogen sulfide. Within a specific range of darkness, the media 600 will turn dark at a linear rate when a constant flow rate and sample concentration are passed through the sample chamber 250.

Correct calibration requires that the parameters of the analyzer 100 be set such that operation is always within the linear range of darkness of the media 600. For example, if the media 600 darkens past the linear range during a particular run, the data acquired will typically be lower than the actual data.

Media darkness is measured by the photocell 310. The photocell 310 provides a signal which is amplified by the amplifiers 402, 404 offset by control 406 and provided to the A/D converter 430. In the presently preferred embodiment, the input voltage from the amplifier 404 is maintained within the range of $-5$ volts to $+5$ volts. The input voltage is converted by the A/D converter 430 into a proportional number of "counts." In the presently preferred embodiment, the proportional number of counts is determined by assigning a $-5$ volt value to 0 counts and a $+5$ volt value to 262,144 counts. Thus, input voltages greater than 5 volts will cause the A/D converter 430 to signal an over range. Input voltages less than $-5$ volts cause the A/D converter 430 to signal an under flow. Tape darkness is monitored on the display 520 during normal operation as "% of scale" readings. Thus, a 0% of scale is the lowest reading before an under flow range is reached and 100% of scale is the highest reading before an over flow range is engaged. One skilled in the art can appreciate that additional apparatus and methods may be used as the converter 430, as well as different voltage ranges and count assignments.

Figure 16:
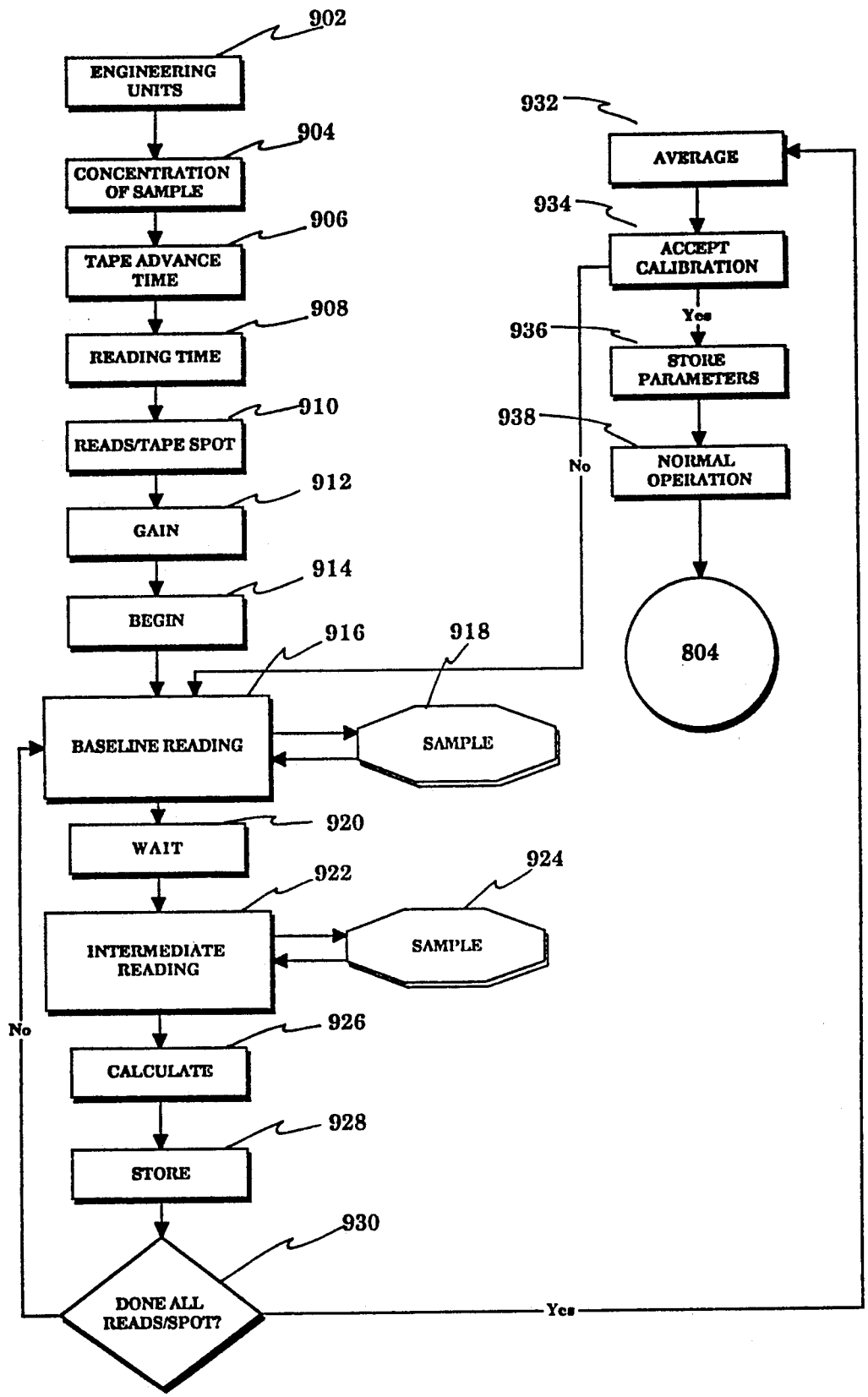
FIG. 16 is a flow diagram illustrating a typical calibration cycle as practiced in one embodiment of the present invention.

FIG. 16 is a flow diagram illustrating the presently preferred calibration sequence for one embodiment of the present invention. At the beginning of each calibration run certain information is input into the apparatus 100. First an operator inputs the data using the magnetic switches 510 and the read out 520. First, the engineering units are input (902). The engineering units can be in ppm, ppb, % or the like. The concentration of the sample upon which the calibration run is made is input (904). To determine how long each roll of media will last, the tape advance time is provided for analysis (906). The reading time is input (908) as well as the number of reads per tape spot (910). Finally, the gain is appropriately set (912). Specifics concerning the various input data is given at other locations herein. The calibration procedure is begun (914). A first base line reading is determined (916). The determination of the first base line reading comprises taking a predetermined number of samples for the particular reading (918). Similar to the operation as described above, one embodiment of the calibration of the present invention provides that seven samples are taken to establish data for a single reading. Preferably the samples taken (918) are acquired in rapid succession. Obviously alternate embodiments can require that samples be taken in other ways, including for example delayed sampling, patterned sampling and the like. After the specified number of samples are taken, a reading is calculated (916). The first base line reading (916) is the average of the samples taken (918). A predetermine period of time is allowed to pass (920). A second intermediate reading is determined (922). The determination of the second intermediate reading (922) comprises taking a predetermined number of samples for the intermediate reading (922). Again, in one embodiment, the samples are acquired (924) in rapid succession. After the specified number of samples are taken, the intermediate reading is calculated (922). The second intermediate reading is the average of the samples taken (924). A change in darkness calculation is made (926). The change in darkness calculation (926) utilizes the first base line reading (916) and the second intermediate reading (922) and the predetermined period of time between readings (920). The darkness reading is stored in memory (928). It is determined whether all of the reads per tape spot as previously set (910) has been accomplished (930). If not, the calibration technique transfers back to calculating another base line value (916). If all the reads per tape spot have been accomplished, an average of the change in darkness values (926) is made (932). The operator can accept or reject the calibration (934) if the calibration is accepted, all the calibration parameters are appropriately stored (936). Thereafter, the apparatus of the present invention proceeds to normal operation (938). Normal operation is discussed herein and illustrated in FIG. 12.

Based upon the base line reading $R_1$ and the second reading $R_2$, a calibration, CAL, can be derived. Preferably, the calibration formula is:

$$CAL = \frac{CC(R_2 - R_1)}{CR}$$

where:
CAL = calibration;
CC = calibration constant—a value keyed into the analyzer by the operator which is expressed in ppm, ppb or percent;
$R_1$ = base line reading—average of seven readings at beginning of reading period, expressed in counts;
$R_2$ = final reading—average of seven readings at end of reading period, expressed in counts; and
CR = calibration reading—the number of counts calculated by the analyzer as the response to known calibrated standard fluid.

The base line and second reading in the calibration procedure has an average of seven different values taken in quick succession. This technique is used in an effort to reduce the uncertainty of the readings and lower the analyzer noise. A method of reducing analyzer noise is to set the analyzer to acquire the largest possible count difference between the base line reading and the second reading. The increased count difference can be accomplished by changing the gain 408 of the analyzer 100. In the present preferred embodiment of the analyzer 100, four different gain settings are possible.

Also, resolution should be considered in making the calibration measurement. Resolution is a measure of what degree of fineness the quantity under investigation can be measured. In the present invention, if a 1000 ppb sample was generating 100 counts, you could measure this sample to a resolution of $+/-10$ ppb. If that same sample could generate 1000 counts, you could measure the sample to a resolution of $+/-1$ ppb, in other words, ten times finer. For example, when measuring low concentrations with the present invention, the media 600 may not get dark at a fast rate over the course of a run. This is caused by the fact that at low gain settings, the number of counts per reading will be low. It is important to consider the increase of the gain in an effort to increase the number of counts. The apparatus of the present invention has sufficient gain available to generate signals from the photocell 310 that can drive the A/D converter 430 to a full scale position even if the media 600 darkness is only imperceptible during a run. Thus, the present analyzer has extraordinary sensitivity.

The smallest concentration determinable by the present invention is limited by the measurement uncertainty. The measurement uncertainty is where the difference signal is the same as the noise of the system. The range of darkness that the photocell can detect for a given gain without causing an over range or under flow is called the detection window. The second goal of calibration is to use as much of the detection window as possible for a given calibration. Detection window gain can be readily determined. The detection window gain is based on the "greatest most likely concentration" expected to be read by the analyzer 100. The greatest most likely concentration can have broad interpretations depending on the application. Some applications of the present invention require that any sample concentration of fluid encountered be on scale and measurable. Other applications would require that the gain be set such that a certain maximum concentration would be on scale and readable, but very large upset concentrations can go off scale without causing problems with the calibration.

Gain and reading time are typically set such that a standard fluid sample of the greatest most likely concentration will generate a tape darkness of no greater than 95% of scale during a run. The zero base line is set so that the display shows 5% of scale for a freshly updated portion of the reflective sensing media 600. Similarly, reading time and number of readings per tape segment can also be adjusted to optimize the calibration range.

Several parameters must be considered because they sufficiently affect calibration. As previously discussed, the type of sample chamber 250 directly effects the calibration. A wedge, open or diffuser sample chamber can be used depending on the requirements as discussed herein. Also, the gain must set as previously discussed. Typically, it is best to use the lowest gain setting practical for a given application. Adjustments to the gain control 408 should be made in conjunction with adjustments to the reading time. Adjustment of the readings per reflective sensing media segment should be made to optimize the present invention with respect to noise, response time and reflective sensing media life. Preferably, reading time can be adjusted from 1 second per reading to 99 seconds per reading. Times less than 10 seconds are used for higher concentrations. Times greater than 10 seconds are used for low concentrations. The reading time parameter affects the analyzer response time as well as the reflective sensing media usage. The number of readings at a single spot of media 600 can successfully accomplish is dependent upon the concentration of the sample under investigation. For single ppm concentrations and below, it is advantageous to increase the number of readings per media spot to save media. Also, increasing the number of readings per media spot minimizes noise. The optimum number of readings per media segment should be determined experimentally for each application, response time and media life requirements. The flow through the sample chamber 250 is preferably about 1 to 300 milliliters per minute. Lowering the sample flow through the sample chamber 250 can lower the response of the analyzer 100 to any given concentration. Also, lowering the sample flow increases the response time of the analyzer.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. An apparatus for measuring the concentration of a fluid in a process stream or environment comprising:
    (a) a fluid sensing means comprising,
        (1) a reflective sensory media which changes reflectivity at a rate indicative of the concentration of the fluid engaged with said media,
        (2) a cassette for securing and dispensing said media, and
        (3) a sample chamber in operative association with said cassette for receiving the fluid and engaging the fluid with said media,
    (b) an optic transmission means comprising,
        (1) a source for generating light in a range of frequencies for enhancing the change of reflectivity of the reflective sensing media,
        (2) a detector for receiving and gauging the light intensity and for generating an analog signal characteristic thereof, and
        (3) an optic fibre cable for directing the light from said source to said media and for accepting the reflected light from said media for directing the reflected light to said detector,
    (c) a signal processing means comprising
        (1) an amplifier for receiving and amplifying the analog signal from said detector,
        (2) a converter for receiving and changing the amplified analog signal to a digital signal, and
        (3) a computer for receiving the digital signal calculating the concentration of the fluid based upon the rate of change of the reflectivity of said media, and
    (d) an interface comprising
        (1) one or more switches for communicating with said computer to input calibration and operating parameters,
        (2) a display for representing the concentration of the fluid calculated by said computer and for representing the calibration parameters input via said switches, and also representing changeable labels of said switches.

2. An apparatus for measuring the concentration of a fluid in a process stream or environment as defined in claim 1 further comprising an explosion-proof containment for protecting the apparatus.

3. An apparatus for measuring the concentration of a fluid in a process stream or environment as defined in claim 2 wherein said switches are enclosed in said explosion-proof containment and communication with said switches is via a magnet.

4. A method of calibrating an apparatus for measuring the concentration of a fluid in a process stream or environment comprising the steps of:
    (a) inputting into the apparatus the appropriate engineering units,
    (b) inputting into the apparatus the concentration of a sample previously attached upon which the calibration is to be made,
    (c) inputting into the apparatus the tape advance time,
    (d) inputting into the apparatus the reading time,
    (e) inputting into the apparatus the number of reads per tape spot,
    (f) inputting into the apparatus the gain, (g) initiating the calibration procedure,
(h) determining a first baseline reading comprising
  (1) determining the number of samples for the particular reading,
  (2) taking the samples in rapid succession, and
  (3) calculate the reading by averaging the sample over time,
(i) waiting a predetermined period of time
(j) determining a second intermediate reading comprising
  (1) determining the number of samples for the particular reading,
  (2) taking the samples in rapid succession, and
  (3) calculate the reading by averaging the sample,
(k) calculating a change in darkness value in engineering units
(l) storing the darkness reading in the apparatus,
(m) determining whether all of the reads per tape spot, as previously set, has been accomplished,
(n) if all of the reads per tape spot have not been accomplished, returning to step (h) for determining a first baseline reading,
(o) if all of the reads per tape spot have been accomplished, averaging the change in darkness values previously made,
(p) accepting or rejecting the calibration,
(q) if the calibration is rejected, repeating the calibration,
(r) if the calibration is accepted, storing the calibration parameters in the apparatus, and
(s) proceeding to normal operation.

* * * * *